(12) United States Patent
Takaki et al.

(10) Patent No.: US 8,168,780 B2
(45) Date of Patent: May 1, 2012

(54) METHOD FOR PRODUCING A SPECIFIC POLYMORPH OF TITANYLPHTHALOCYANINE

(75) Inventors: Kenji Takaki, Neyagawa (JP); Yasuhiro Yamasaki, Neyagawa (JP)

(73) Assignee: Orient Chemical Industries, Ltd., Osaka-Shi (JP)

( * ) Notice: Subject to any disclaimer, the term of this patent is extended or adjusted under 35 U.S.C. 154(b) by 1038 days.

(21) Appl. No.: 12/076,352

(22) Filed: Mar. 17, 2008

(65) Prior Publication Data

US 2008/0305419 A1 Dec. 11, 2008

(30) Foreign Application Priority Data

Mar. 23, 2007 (JP) ................................ 2007-076598

(51) Int. Cl.
*C09B 47/04* (2006.01)
(52) U.S. Cl. ...................................................... 540/140
(58) Field of Classification Search .................... 540/140
See application file for complete search history.

(56) References Cited

U.S. PATENT DOCUMENTS 5,350,844 A * 9/1994 Martin et al. ................. 540/141

FOREIGN PATENT DOCUMENTS

| EP | 0 482 922 | 4/1992 |
|----|-----------|--------|
| JP | 63-37163 A | 2/1988 |
| JP | 7-91486 B2 | 10/1995 |
| JP | 9-87540 A | 3/1997 |
| JP | 11-021466 | 1/1999 |
| JP | 2001-296676 A | 10/2001 |

* cited by examiner

*Primary Examiner* — James O Wilson
*Assistant Examiner* — Brian McDowell
(74) *Attorney, Agent, or Firm* — Birch, Stewart, Kolasch & Birch, LLP (57) ABSTRACT

The present invention provides a method for producing a polymorphic form of a titanylphthalocyanine having superior photoreceptor characteristics, particularly superior charge-ability and photosensitivity to those of the conventional titanylphthalocyanines.

5 Claims, 5 Drawing Sheets

METHOD FOR PRODUCING A SPECIFIC POLYMORPH OF TITANYLPHTHALOCYANINE

TECHNICAL FIELD

The present invention relates to a titanylphthalocyanine comprising a specific polymorph and a method for producing the titanylphthalocyanine as well as an electrophotographic photoreceptor comprising a charge generating material of a titanylphthalocyanine comprising a specific polymorph.

BACKGROUND OF THE INVENTION

In image-formation apparatuses, such as photocopiers and printers, to which electrophotographic technologies are applied, many organic photoreceptors are employed, each of which has a sensitivity to light emitted from a light-source in the apparatus within a range of wavelength of the light. It is known that the organic photoreceptor includes monolayer type photoreceptors and multilayer type photoreceptors. The monolayer type photoreceptor comprises a single photoreceptor layer wherein a charge generating material and a charge transferring material have been dispersed in a thin film of an appropriate binder resin. The multilayer type photoreceptor comprises a charge generating layer comprising a charge generating material; and a charge transferring layer comprising a charge transferring material, wherein the charge generating layer and the charge transferring layer are laminated.

Conventional phthalocyanine compound has a spectral sensitivity to a light having a long wavelength or less, good charge generation efficiency, good fastness, high sensitivity and high durability. Therefore, various phthalocyanine compounds are employed as charge generating materials. Among others, titanylphthalocyanine can be used in an electrophotographic photoreceptor, since the titanylphthalocyanine has characteristics such as high charging amount and high sensitivity, and the titanylphthalocyanine can be easily formed into a thin film, such as a charge generating layer, by vapor deposition or dispersing.

These phthalocyanine compounds have considerably different electric characteristics depending on each stacking state even though they have the same molecular structure. Stacking state of the organic compound molecule is determined by polymorph. Therefore, different polymorph provides different stacking state. Accordingly, perturbation of electron in π electron system is altered. This is why that the characterists in an electronic material such as an organic photoreceptor can be significantly altered.

Generally, titanylphthalocyanines can be produced by an urea method (Weiller method) or a phthalonitrile method. These conventional methods, however immediately after the synthesis, often provide a crude titanylphthalocyanines containing various polymorphs, such as "β-type", "α-type" and other metastable polymorphs, i.e., a polymorphic mixture. Since the polymorphic mixture is a mixture of crystals each of which has different electric characteristics, the conventional titanylphthalocyanines are not suitable for applying to a charge generating material such as an electrophotographic photoreceptor.

Titanylphthalocyanine having a suitable single polymorph has been investigated in order to use the titanylphthalocyanine as a crude in a charge generating material. Examples of such trials include the follows.

Patent Literature 1: JP-B-7-91486 discloses a crystalline oxytitanium phthalocyanine, i.e., titanylphthalocyanine crystal, which has a maximum diffraction peak at Bragg angle ($2\theta\pm0.2°$) of 27.3°, in X-ray diffraction spectrum, and other diffraction peaks at Bragg angles of 7.4°, 9.7° and 24.2°. In addition, Patent Literature 1 further discloses that the titanylphthalocyanine is used as a charge generating material, and the charge generating material has good characteristics such as sensitivity, chargeablitiy, dark decay and residual potential.

Patent Literature 2: JP-A-63-37163 discloses a method for transforming a crystal form, which includes a step of pulverizing a B-type crystal of an oxytitanium phthalocyanine, in the presence of an A-type crystal thereof, in an organic solvent to transform the B-type crystal of the oxytitanium phthalocyanine into A-type crystal thereof.

Patent Literature 3: JP-A-9-87540 discloses a method for producing a titanylphthalocyanine crystal, which includes a step of contacting a dihalogenotitanium phthalocyanine with an acid having pKa of 5 or less, and then, in the presence of water, with an organic solvent having a specific inductive capacity of 20 or less. Crystal form of TiOPc is a so-called D-type crystal form. The Patent Literature 3 also discloses the crystal form has strong diffraction peaks at Bragg angles ($2\theta\pm0.2°$) of 9.7°, 24.1° and 27.3°, in powder X-ray diffraction spectrum with CuK α-ray, and usually has a maximum diffraction peak at Bragg angle of 27.3°.

Patent Literature 4: JP-A-2001-296676 discloses a positively charged-type electrophotographic photoreceptor, which comprises a photoreceptor layer comprising a conductive substrate and a crystalline titanylphthalocyanine on the conductive substrate which has a maximum diffraction peak at Bragg angle ($2\theta\pm0.2°$) of 27.3°, in X-ray diffraction with CuK α-ray. The electrophotographic photoreceptor is subjected to an exposure with a monochromatic light having wavelength of 600 nm or less to form an image.

SUMMARY OF THE INVENTION

Disclosure of the Invention
Problem to be Solved by the Invention

Although the titanylphthalocyanine disclosed in Patent Literature 1 can be used as a charge generating material for an electrophotographic photoreceptor, such electrophotographic photoreceptor has deficiencies such as poor environmental stability and decreased chargeability.

The procedures disclosed in Patent Literature 4 are complicated and require severe conditions for the production. Therefore, such electrophotographic photoreceptor can not be easily produced in a low cost and in a good reproducibility. In addition, the titanylphthalocyanine disclosed in Patent Literature 4 also has an insufficient sensitivity. Therefore, those skilled in the art desire superior photoreceptor characteristics.

In view of the above problems in the prior arts, the present inventors intensively investigated in order to provide a novel titanylphthalocyanine comprising, a polymorph having a peak at a Bragg angle ($2\theta\pm0.2°$) in X-ray diffraction spectrum with CuK α-ray: 9.0°, 9.6°, 14.1°, 14.9°, 17.9°, 18.3°, 23.4°, 24.5° and 27.2°, and a specific ratio between intensities of the peaks. Therefore, first object with respect to the present invention consists in a provision of a novel titanylphthalocyanine having superior photoreceptor characteristics, particularly in chargeability and photosensitivity to the conventional titanylphthalocyanines. Second object with respect to the present invention consists in a provision of a method for producing a novel titanylphthalocyanine in a convenient manner. In addition, third object with respect to the present invention consists in a provision of an electrophotographic photoreceptor comprising a charging generating material of a novel titanylphthalocyanine, which can provide superior photosensitive characteristics.

Means for Solving the Problem

In order to solve the above problems, the present invention provides a titanylphthalocyanine represented by the formula (1):

(1)

comprising a polymorph having a peak at a Bragg angle (2θ+0.2°) in X-ray diffraction spectrum with CuK α-ray: 9.0°, 9.6°, 14.1°, 14.9°, 17.9°, 18.3°, 23.4°, 24.5° and 27.2°; and $1.3 < I_{r1} < 1.8$;
$1.0 < I_{r2}$;
$1.3 < I_{r3} < 2.0$; and
$0.9 < I_{r4} < 1.1$ wherein $I_{r1}$ is a ratio (9.6°/9.0°) of an intensity of the peak at Bragg angle of 9.6° to an intensity of the peak at Bragg angle of 9.0°;

$I_{r2}$ is a ratio (14.1°/14.9°) of an intensity of the peak at Bragg angle of 14.1° to an intensity of the peak at Bragg angle of 14.9°;

$I_{r3}$ is a ratio (17.9°/18.3°) of an intensity of the peak at Bragg angle of 17.9° to an intensity of the peak at Bragg angle of 18.3°; and $I_{r4}$ is a ratio (24.5°/23.4°) of an intensity of the peak at Bragg angle of 24.5° to an intensity of the peak at Bragg angle of 23.4°.

Furthermore, in order to solve the second problem, the present invention provides a method for producing a titanylphthalocyanine comprising a polymorph having a peak at a Bragg angle (2θ±0.2°) in X-ray diffraction spectrum with CuK α-ray: 9.0°, 9.6°, 14.1°, 14.9°, 17.9°, 18.3°, 23.4°, 24.5° and 27.2°, which includes steps of:

(I) subjecting a titanylphthalocyanine having an α-type polymorph to an acid pasting treatment to give a titanylphthalocyanine in a form of a water-containing cake;

(II) adding a dispersing aid to the resulting titanylphthalocyanine and dispersing at room temperature, in a mixed solvent of water and an organic solvent, to prepare a polymorph, wherein stirring conditions for the dispersing at room temperature are set to give a required stirring power of no less than 3.0 [kg-m/sec]; and (III) filtering, washing, and drying under a reduced pressure.

According to the method for producing the titanylphthalocyanine according to the present invention, it is preferable that the titanylphthalocyanine obtainable/obtained in the step (I) is a low crystalline titanylphthalocyanine.

Furthermore, according to the method for producing the titanylphthalocyanine according to the present invention, it is more preferable that the low crystalline titanylphthalocyanine has a peak at a Bragg angle (2θ±0.2°) in X-ray diffraction spectrum with CuK α-ray: 7.0°, 23.5° and 25.5°.

In addition, in order to solve the third problem, the present invention provides an electrophotographic photoreceptor comprising a charge generating material of the present titanylphthalocyanine.

Effect of the Invention

The present invention can provide a titanylphthalocyanine comprising a polymorph having a significantly superior primary characteristics as a photoreceptor, such as chargeability (e.g., high initial charging amount, decreased dark decay rate, improved charge remaining ability, and the like) to the conventional titanylphthalocyanines. Therefore, the present invention can provide a highly sensitive photoreceptor. Furthermore, the present invention can provide a convenient method for producing the present titanylphthalocyanine.

DETAILED DESCRIPTION OF THE INVENTION

Detailed Description of the Preferred Embodiments

Figure 1:
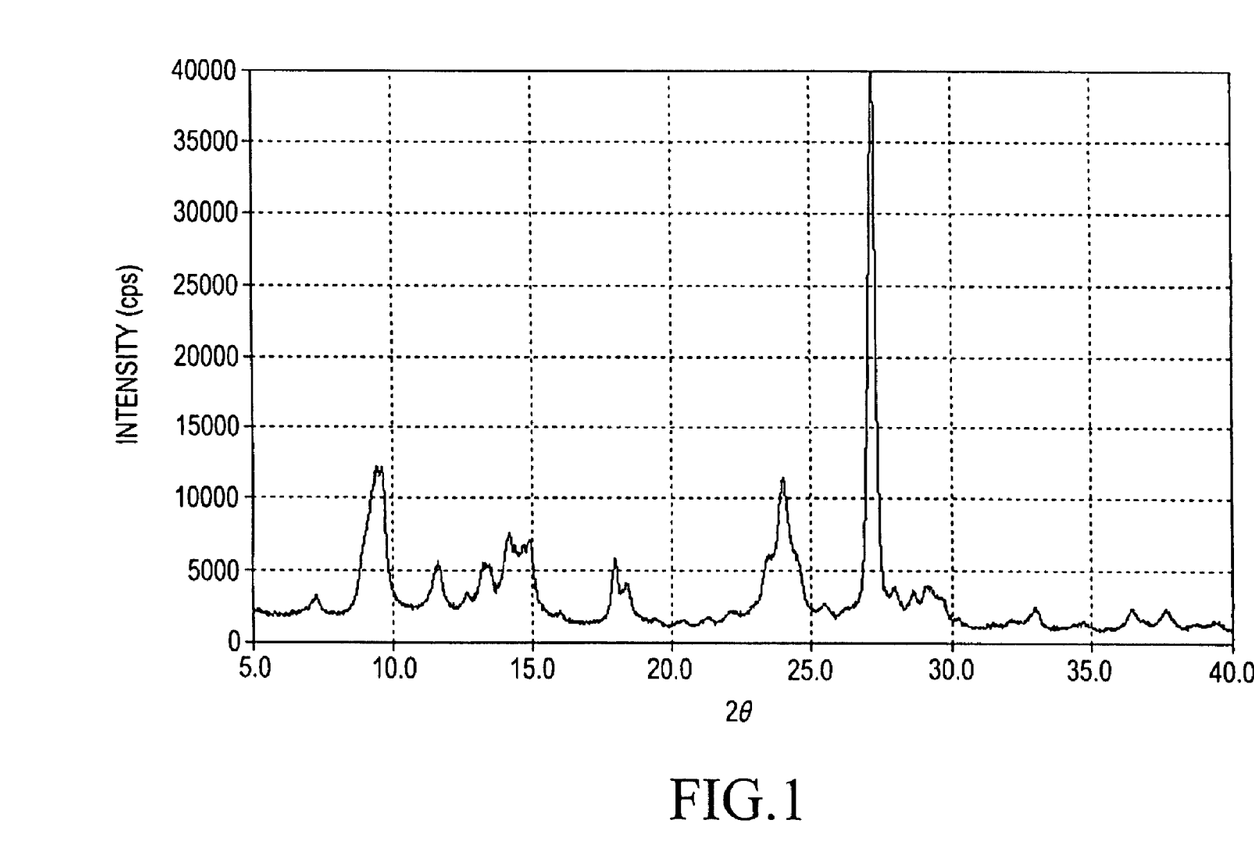
FIG. 1 is an X-ray diffraction spectrum of polymorph of the titanylphthalocyanine according to the present invention.

The titanylphthalocyanine according to the present invention comprises a novel polymorph demonstrated in X-ray diffraction spectrum with CuK α-ray (see FIG. 1; X-ray diffraction spectrum). Herein, the present titanylphthalocyanine comprises a polymorph having peaks at Bragg angles (2θ±0.2°) of 9.0°, 9.6°, 14.1°, 14.9°, 17.9°, 18.3°, 23.4°, 24.5° and 27.2°. The present titanylphthalocyanine has ratios between peak intensities (i.e., $I_{r1}$, $I_{r2}$, $I_{r3}$ and $I_{r4}$) in the following ranges:

$1.3 < I_{r1} < 1.8$;
$1.0 < I_{r2}$;
$1.3 < I_{r3} < 2.0$; and
$0.9 < I_{r4} < 1.1$ wherein $I_{r1}$ is a ratio (9.6°/9.0°) of an intensity of the peak at Bragg angle of 9.6° to an intensity of the peak at Bragg angle of 9.0°;

$I_{r2}$ is a ratio (14.1°/14.9°) of an intensity of the peak at Bragg angle of 14.1° to an intensity of the peak at Bragg angle of 14.9°;

$I_{r3}$ is a ratio (17.90/18.3°) of an intensity of the peak at Bragg angle of 17.9° to an intensity of the peak at Bragg angle of 18.3°; and $I_{r4}$ is a ratio (24.50/23.4°) of an intensity of the peak at Bragg angle of 24.5° to an intensity of the peak at Bragg angle of 23.4°.

The present titanylphthalocyanine comprises a completely different polymorph from those of the conventional titanylphthalocyanines.

The present titanylphthalocyanine comprising the polymorph having the ratios between the peak intensities in the above ranges provides superior properties, for example in evaluation of the primary characteristics as a photoreceptor, such as initial charging amount, dark decay rate, residual potential, sensitivity, dispersing stability and the like, to those of the conventional titanylphthalocyanines. As mentioned above, the present novel titanylphthalocyanine having the ratios between the peak intensities in the above ranges is inherently different from the conventional titanylphthalocyanines, and therefore the present invention is useful.

Subsequently, a method for producing a titanylphthalocyanine comprising the polymorph according to the present invention is described below.

According to the method for producing the titanylphthalocyanine according to the present invention, a titanylphthalocyanine, as a starting material, can be synthesized or produced by any one of conventionally known methods such as a urea method and a phthalonitrile method. Herein, the polymorph of the starting titanylphthalocyanine may be in α-type, β-type or other metastable type, or in a mixture thereof. α-type titanylphthalocyanine is preferable to produce the titanylphthalocyanine according to the present invention with a high accuracy. With respect to the method for producing a starting titanylphthalocyanine, it is more preferable to use a phthalonitrile method, since the phthalonitrile method can generally provide the starting titanylphthalocyanine in a higher yield and a higher purity than those in the other methods such as urea method.

Generally, the titanylphthalocyanine having α-type polymorph, which can be preferably used as a starting titanylphthalocyanine, can be prepared in a known method including a condensation of phthalonitrile with a metal compound (e.g., titanium tetrachloride) in an aromatic solvent having a high boiling point (e.g., quinoline, α- or β-chloronaphthalene, α-methylnaphthalene and nitrobenzene); hydrolysis; and then washing with a solvent such as DMF.

According to a routine procedure, the starting titanylphthalocyanine can be subjected to an acid pasting treatment (which is, hereinafter, referred to as Step (I)). The acid pasting treatment is a conventional procedure to purify and finely divide a crude titanylphthalocyanine. Generally, the acid pasting treatment includes steps of dissolving the titanylphthalocyanine in an acid such as a concentrated sulfuric acid; and then pouring the solution into a large amount of water to reprecipitate the titanylphthalocyanine.

Herein, the acid to be used for the acid pasting treatment is preferably concentrated sulfuric acid. When the concentrated sulfuric acid is used as the acid, the concentration of the concentrated sulfuric acid is generally within a range of from 80 to 100%, and preferably within a range of from 95 to 100%. The amount of the concentrated sulfuric acid to be used is not particularly limited with the proviso that the amount is enough to provide a good paste suitable for subjecting to the following purification and finely dividing.

Figure 2:
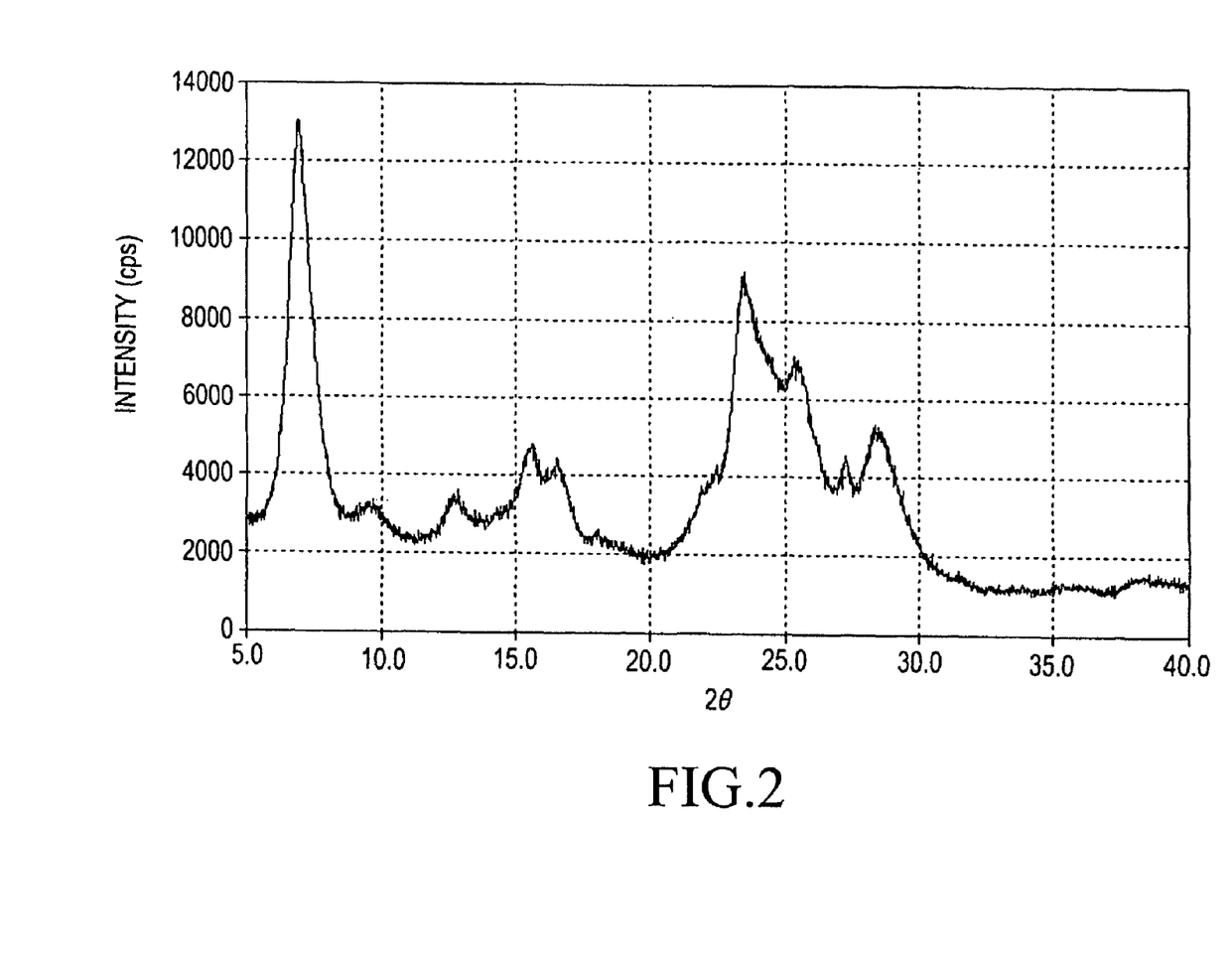
FIG. 2 is an X-ray diffraction spectrum of the low crystalline titanylphthalocyanine after acid pasting treatment.

The resulting titanylphthalocyanine after the acid pasting treatment is a low crystalline titanylphthalocyanine having peaks at Bragg angles (2θ±0.2°) in X-ray diffraction spectrum with CuK α-ray: 7.0°, 23.5° and 25.5°, for example, as shown in FIG. 2. The acid pasting treatment can facilitate the following transformation step with a mixed solvent of water and an organic solvent.

The resulting low crystalline titanylphthalocyanine after the acid pasting treatment is need to be sufficiently washed with water (e.g., ion-exchange water and distilled water), and if necessary, dried. The titanylphthalocyanine can be employed in the following step in a dried state or in a water-paste state (i.e., a water-containing cake (or a wet cake)). The washing with water is preferably carried out until pH of the used wash water falls within a neutral pH range.

Subsequently, the low crystalline titanylphthalocyanine, preferably in a water-containing cake (wherein water content is within a range of from 50 to 95%) is subjected to a transformation step with a mixed solvent of water and an organic solvent (which is, hereinafter, referred to as Step (II): preparation of polymorph). Herein, it is preferable to use a dispersing aid such as glass beads, steel beads and alumina beads. Among others, glass beads are more preferably used. The particle size of the dispersing aid is generally within a range of from 0.1 to 10 mm, and preferably within a range of from 0.3 to 5 mm. The dispersing aid which can be used in the present invention is not limited to the above-described dispersing aids.

The amount of the dispersing aid to be used is, but is not particularly limited to, an amount within a range of from 10 to 100%, and preferably within a range of from 40 to 60%, based on total of weight of water in the water-containing cake of the titanylphthalocyanine (water content: 50 to 95%) and weight of the mixed solvent of water and an organic solvent.

According to the present invention, the organic solvent contained in the mixed solvent of water and the organic solvent, which may be employed in the transformation step, includes, but is not particularly limited to, an organic solvent which can not dissolve the titanylphthalocyanine and which depends on the desired polymorph, such as monohydric lower alcohol solvents such as methanol, ethanol, propanol and isopropanol; linear or cyclic ether solvents such as THF, diethyl ether and dioxane; and hydrocarbon solvents such as n-hexane, n-heptane, n-octane, cyclohexane, methylcyclohexane, benzene, toluene, xylene, and tetralin; etc.

According to the present invention, the mixing ratio of water to the organic solvent in the mixed solvent (water/organic solvent), which may be employed in the transformation step, is within a range of from 1/80 to 50/80 and preferably within a range of from 2/80 to 20/80 as a basis of volume.

In the transformation step according to the present invention, conventionally known apparatuses may be employed. For example, the apparatuses include a reaction vessel which can be used in a general synthetic reaction. In addition, apparatuses such as a sand mill, an attritor, a roll mill and a homomixer may be used.

According to the transformation step in the present invention, it is necessary that the dispersing aid is added to the titanylphthalocyanine obtained in the above-described previous step, in the presence of a solvent, in the above-described apparatus to give a mixture; the mixture is stirred and dispersed at a constant stirring efficacy or more; kinetic energy due to shearing stress to the dispersing medium is transferred to the titanylphthalocyanine to prepare a polymorph.

Figure 3:
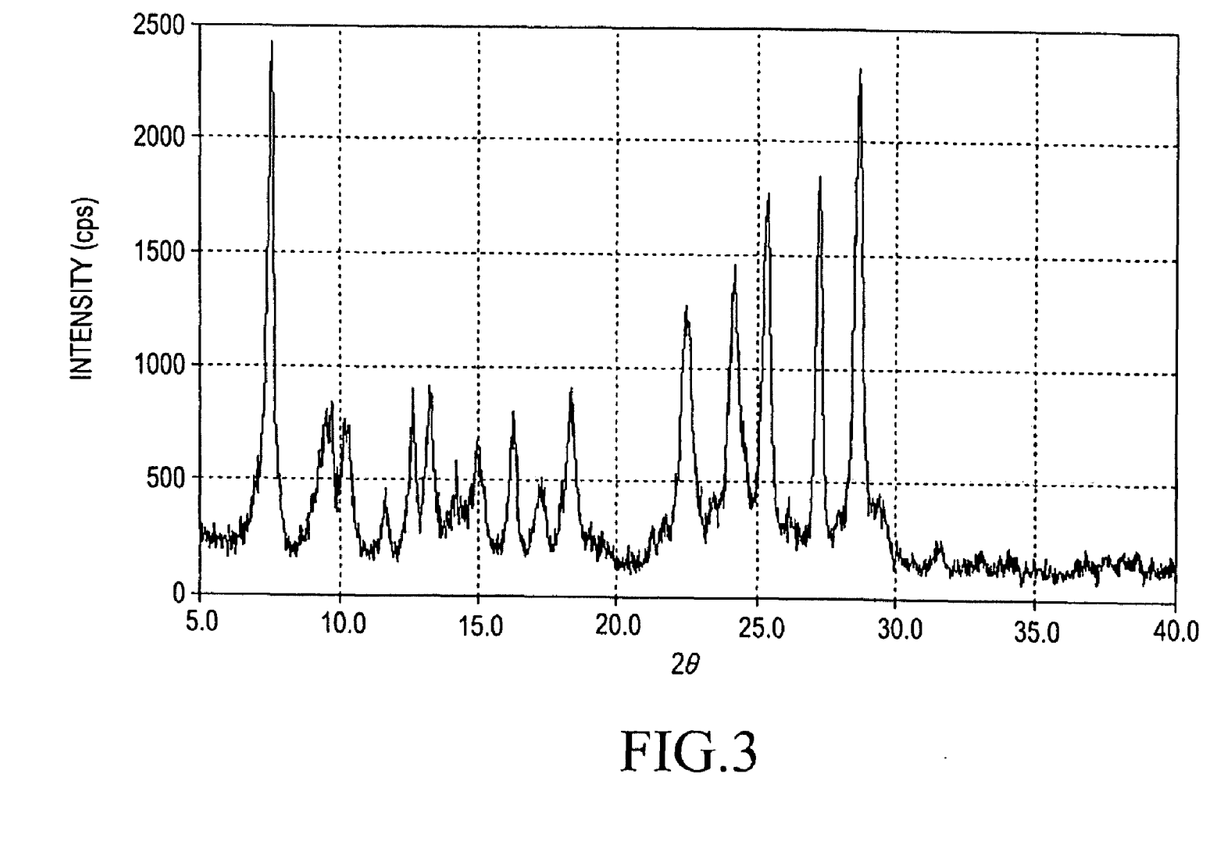
FIG. 3 is an X-ray diffraction spectrum of the titanylphthalocyanine obtained in Comparative Example 1, as a mixture of α-type and γ-type polymorphs.

Required stirring power P [kg-m/sec] is known as an index for the polymorph, which can be calculated from a resistance force of a liquid, which is associated with rotation of stirring blade equipped with in the above-described apparatus ("Elementary Chemical Engineering" edited by Chemical Engineering Society (published form Meibun Shobo); and "Stirring Technologies" edited by Satake Kagaku Kikai Kogyo, K. K., supervised by Yamamoto and Nishino, 1992). Control of the required stirring power allows the low crystalline titanylphthalocyanine to be converted to the polymorph according to the present invention. In the case that the required stirring power is low, the conventional titanylphthalocyanines are resulted with a frequent reproducibility, each of which has known polymorph exhibiting X-ray diffraction spectrum as shown in FIG. 3.

The required stirring power can be influenced on the following four groups of factor(s):

1) Factors associated with stirring blade: blade length d [m]; blade width b [m]; angle of blade (i.e., slope angle relative to rotation plane) θ; rotation rate: N [1/sec];

2) Factors associated with cylindrical stirring vessel: vessel diameter D [m]; depth (from the liquid surface to the vessel bottom) H [m];

3) Factors associated with stirred liquid: density ρ[kg/m$^3$], viscosity μ[kg/m·sec];

4) Acceleration of gravity g [m/sec$^2$].

With respect to other parameters such as mounting height, these parameters can be approximated and taken as an approximation (i.e., zero), wherein it is considered that the stirring vessel and stirring blade are conformable. Taking into consideration of these parameters, required power number: Pgc is adoptable to the calculation of the required stirring power. Herein, power number: Np is generally represented by the following equation (2), which is a function ($f_2$):

$$Np = Pgc/\rho N^3 d^5 = f_2(Re, Fr) \qquad (2)$$

wherein
Re is Reynolds number, and
Fr is Field number.
Accordingly, the required stirring power: P is represented by the following equation (3).

$$P = Np \cdot \rho N^3 d^5 / g \qquad (3)$$

Particularly in the case of a paddle type stirring blade, as an experimental equation, the power number: Np is also represented by the following equation (4):

$$Np = A/Re + B\{(10^3 + 1.2Re^{0.66})/(10^3 + 3.2Re^{0.66})\}^p$$
$$(H/D)^{0.35 + b/D}(\sin\theta)^{1.2} \qquad (4)$$

wherein Re, A, B and p are independently represented by the following equations (5) to (8).

$$Re = d^2 N\rho/\mu \qquad (5)$$

$$A = 14 + (b/D)[670(d/D - 0.6)^2 + 185] \qquad (6)$$

$$B = 10\hat{0}[1.3 - 4(d/D - 0.5)^2 - 1.14(d/D)] \qquad (7)$$

$$p = 1.1 + 4(b/D) - 2.5(d/D - 0.5)^2 - 7(b/D)^4 \qquad (8)$$

The required stirring power to be used in the present invention is derived from the above equations. Herein, it should be noted that the stirring blade which may be used in the present invention is not limited to the paddle type.

According to the present invention, the preparation of the polymorph needs the required stirring power of no less than 3.0 [kg-m/sec]. If the required stirring power is less than 3.0 [kg-m/sec], the transfer of energy to the substrate is insufficient and the resulting polymorph is insufficient to give a conventional titanylphthalocyanine having a conventional polymorph. The required stirring power is preferably within a range of from 3.0 to 15 [kg-m/sec], and more preferably within a range of from 3.0 to 7.5 [kg-m/sec].

The transformation step is carried out at room temperature (usually within a range of from 15 to 40° C.) for no less than 10 hours, and preferably within a range of from 10 to 50 hours. If time for the transformation step is less than 10 hours, the formation of the desired polymorph is insufficient. Whereas, even if time for the transformation is more than 50 hours, generally, significant effects cannot be asserted. This transformation procedure can facilitate the growth of the polymorph according to the present invention. Therefore, the resulting titanylphthalocyanine comprising the novel polymorph can provide excellent photosensitive characteristics. Herein, the transformation procedure is sometimes referred to as "dispersing at room temperature".

The dispersing aid is removed off after the transformation procedure. The removing means include, but are not particularly limited to, those can only remove off the used dispersing aid. It is preferable to use a sieving screen having pores each of which has a size within a range of from 150 to 300 μm. If the size is less than 150 μm, time is terribly taken long to remove off the dispersing aid and it provides a low yield. Whereas, if the size is more than 300 μm, there may be a contamination of a fragment of the dispersing aid into the resulting titanylphthalocyanine, which can deteriorate the photosensitive characteristics thereof.

Filtering and washing of the resulting suspension removed off the dispersing aid can provide the titanylphthalocyanine having the polymorph according to the present invention. The filtering procedure includes, but is not particularly limited to, a conventional method. The washing procedure is appropriately carried out with an organic solvent such as DMF, THF and methanol; ion-exchange water; distilled water; or the like. Furthermore, the production method according to the present invention includes various known purifying methods. In order to apply the titanylphthalocyanine according to the present invention to an electrophotographic photoreceptor, it is preferable that the titanylphthalocyanine has in a high purity.

It is preferable that the resulting titanylphthalocyanine after filtering and washing procedures is subjected to drying under a reduced pressure. The drying temperature is generally within a range of from 40 to 100° C., and preferably within a range of from 50 to 70° C. Time for drying is within a range of from 15 to 70 hours. After drying, a pulverizing process allows the titanylphthalocyanine according to the present invention to be applied, as a charge generating material, to an electrophotographic photoreceptor.

Accordingly, the present inventive production method can conveniently provide the desired titanylphthalocyanine without any complicated procedures such as washing with a solvent under heating and heat treatment.

Subsequently, the electrophotographic photoreceptor according to the present invention is described hereinafter.

The electrophotographic photoreceptor according to the present invention comprises a charge generating material of a titanylphthalocyanine comprising a polymorph having a peak at a Bragg angle (2θ±0.2°) in X-ray diffraction spectrum with CuK α-ray: 9.0°, 9.6°, 14.1°, 14.9°, 17.9°, 18.3°, 23.4°, 24.5° and 27.2°; and $1.3 < I_{r1} < 1.8$;
$1.0 < I_{r2}$;
$1.3 < I_{r3} < 2.0$; and
$0.9 < I_{r4} < 1.1$ wherein
$I_{r1}$ is a ratio (9.6°/9.0°) of an intensity of the peak at Bragg angle of 9.6° to an intensity of the peak at Bragg angle of 9.0°;

$I_{r2}$ is a ratio (14.1°/14.9°) of an intensity of the peak at Bragg angle of 14.1° to an intensity of the peak at Bragg angle of 14.90;

$I_{r3}$ is a ratio (17.90/18.3°) of an intensity of the peak at Bragg angle of 17.9° to an intensity of the peak at Bragg angle of 18.3°; and $I_{r4}$ is a ratio (24.50/23.4°) of an intensity of the peak at Bragg angle of 24.5° to an intensity of the peak at Bragg angle of 23.4°. The present electrophotographic photoreceptor comprising the titanylphthalocyanine, i.e., the above-described titanylphthalocyanine according to the present invention, as a charge generating material can provide excellent charging characteristics, superior sensitivity, superior durability, and therefore can provide an excellent digital photosensitive characteristics.

In order to provide preferable photosensitive characteristics, the ratio $I_{r2}$ between the certain peak intensities of the above-described titanylphthalocyanine is preferably within a range of $1.0<I_{r2}<2.0$, and more preferably within a range of $1.0<I_{r2}<1.5$.

The electrophotographic photoreceptor comprises a photoreceptor layer comprising the titanylphthalocyanine having the specific polymorph according to the present invention, wherein the photoreceptor layer may have a one-layer structure or a two-layer structure comprising a charge generating layer and a charge transferring layer. In order to significantly present the photosensitive characteristics of the polymorph of the titanylphthalocyanine, it is preferable to apply the titanylphthalocyanine to a photoreceptor having a two-layer structure or a multi-layer structure, wherein each function can be provided in each layer, and wherein a slight amount of generated charges can be intercepted, and therefore the electric charge is effectively transferred to the surface of the photoreceptor without adversely effecting on each function in each layer.

Such photoreceptor in a function separated type can be formed, for example, by laminating a thin charge generating layer and a thin charge transferring layer thereon, in this order, on a conductive support. A material for the conductive support includes a metal such as aluminum and nickel, a metal deposition film thereof, etc. The conductive support can be manufactured in a form of drum, sheet or belt.

A method for adopting the titanylphthalocyanine to an electrophotographic photoreceptor includes an initial step of forming a charge generating layer comprising a charge generating material [i.e., CG material (CGM)] of the titanylphthalocyanine according to the present invention, in a preferable form of a thin film, on a conductive support. Herein, the charge generating layer can be formed by depositing the titanylphthalocyanine on the conductive support, or by applying a coating solution containing the charge generating material to the conductive support, wherein the coating solution can be prepared by dispersing the charge generating material in a solvent to which a binder resin has been dissolved.

The method for dispersing the titanylphthalocyanine includes a conventional dispersing method by means of a ball mill, a sand mill, a paint shaker, or the like.

An applicator for the charge generating layer includes, but is not particularly limited to, for example, a bar coater, a dip coater, a spin coater, a roller coater, and the like, each of which can be appropriately employed. Drying may be carried out, for example, at a temperature within a range of from 30 to 200° C. for 5 minutes to 5 hours with or without an air stream.

The solvent for preparing the coating solution includes, but is not particularly limited to, known organic solvents, which can uniformly disperse the titanylphthalocyanine without dissolving the titanylphthalocyanine, and if necessary which can dissolve the binder resin. Examples of the solvent include alcohol solvents such as methanol, ethanol, isopropanol and butanol; aromatic solvents such as toluene, xylene and tetralin; halogen solvents such as dichloromethane, chloroform, trichloroethylene and carbon tetrachloride; ester solvents such as ethyl acetate and propyl acetate; ether solvents such as ethylene glycol monoethyl ether, dioxane and tetrahydrofuran; ketone solvents such as cyclohexanone, acetone, methyl ethyl ketone and methyl isobutyl ketone; dimethylformamide; dimethylsulfoxide; etc.

The binder resin can be selected from various insulating resins. Preferable binder resin includes condensed resins such as polycarbonates, polyacrylates, polyesters and polyamides; addition polymers such as polystyrenes, styrene/acrylic copolymers, polyacrylates, polymethacrylates, polyvinylbutyrals, polyvinyl alcohols, polyacrylonitriles, polyacryl/butadiene copolymers, polyvinyl chlorides and vinyl chloride/vinyl acetate copolymers; insulating resins such as poly-N-vinylcarbazoles and polyvinylanthracenes; polysulfones; polyethersulfones; silicone resins; epoxy resins; urethane resins; etc. The binder resin may be used in an appropriate combination thereof. Herein, the binder resin which can be used in the present invention is not limited to the above exemplified resins.

The amount of the above-described binder resin to be used is within a range of from 0.1 to 3, in a weight ratio, relative to the weight to the charge generating material. If the weight ratio is more than 3, the concentration of the charge generating material in the charge generating layer may be decreased to provide a deteriorated sensitivity. Film thickness of the charge generating layer is generally within a range of from 0.05 to 5.0 μm, and preferably no more than 10 μm.

Subsequently, a charge transferring layer comprising a charge transferring material [i.e., CT material (CTM)] in a preferable form of a thin film can be formed on the charge generating layer. A method for forming the thin film includes the similar procedures to those in the applying method for the charge generating layer. Herein, the charge transferring material can be dissolved, if necessary together with the binder resin, in a solvent, and the resulting coating solution can be uniformly applied on the charge generating layer and then subjected to drying.

The charge transferring material includes, but is not particularly limited to, known compounds such as an oxadiazoles, pyrazolines, pyrazoles, hydrazones, triazines, quinazolines, triarylamines, methaphenylenediamines, carbazoles, indoles, imidazoles, styryls, styryltriarylamines, butadienes, etc.

The binder resin and solvent for preparing the charge transferring layer include those above-exemplified in the preparation of the charge generating layer, etc.

The amount of the above-described binder resin to be used is within a range of from 0.1 to 5, in a weight ratio, relative to the weight of the charge transferring material. If the weight ratio is more than 5, the concentration of the charge transferring material in the charge transferring layer may be decreased to provide a deteriorated sensitivity. The film thickness of the charge transferring layer is generally within a range of from 5 to 100 μm. If the film thickness is more than 100 μm, the transferring of the electric charge takes much more time, and the electric charge can be trapped in a certain high probability, and therefore which can cause an undesired deteriorated sensitivity.

EXAMPLES

Hereinafter, the present invention is further described in detail in the following Examples, which are not intended to limit the present invention.

Herein, the density ρ and the viscosity μ are parameters for determining the above-described required stirring power for preparing the polymorph according to the present invention. The density ρ is a constant: 1338 [kg/m$^3$] and the viscosity μ is also a constant: 0.25 [kg/m·sec], since all the reaction conditions require a single charging ratio.

Example 1

Step (1-A): Preparation of α-type Titanylphthalocyanine
100 g (0.780 mol) of o-phthalonitrile and 1 L of quinoline were charged into a 2 L separable flask. The mixture was stirred in a nitrogen atmosphere. 84.98 g (0.448 mol) of titanium tetrachloride was added to the mixture. Subsequently, the mixture was heated to 180° C. and stirred with heating at the same temperature for 6 hours. After the reaction was completed, the temperature in the system allowed to be decreased to 150° C., and then the reaction mixture was filtered with heating. Subsequently, 1 L of DMF heated (at 110° C.) was added to and washed the residue.

The resulting wet cake was added to 640 ml of DMF and dispersed at 130° C. for 2 hours. The dispersion was filtered with heating at 130° C. Subsequently, 1 L of DMF was added to and washed the residue. This routine procedure was repeated four times. Subsequently, 1 L of methanol was added to and washed the resulting residue. The resulting wet cake was dried at 40° C. under a reduced pressure to give a blue solid (in Producing amount: 86.3 g and Yield: 76.8%).

Step (1-B): Acid Pasting Treatment 900 g of concentrated sulfuric acid was cooled to no more than 3° C. in an ice-methanol bath. 30 g (52 mmol) of the above-prepared blue solid was added into the concentrated sulfuric acid with keeping the temperature at no more than 5° C. The reaction mixture was stirred at no more than 5° C. for 1 hour, and then the reaction mixture was added dropwise to 9000 ml of water and 1000 ml of ice so that the temperature in the system did not exceed 5° C. The mixture was dispersed at room temperature for 2 hours, and then the dispersion was allowed to be left and past trough a filter. The resulting cake was added into 6000 ml of water, and then dispersed at room temperature for 1 hour. Subsequently, the dispersion was allowed to be left and past trough a filter. This routine procedure was repeated three times. The resulting cake was added into 5000 ml of water, dispersed at room temperature for 1 hour, and then allowed to be left and past trough a filter. This routine procedure was repeated twice, and then 2000 ml of ion-exchange water was added to and washed the residue. Once pH>6.0 and electroconductivity<20 μS, the wet cake was taken up. Producing amount: 91 g (water content: 72%) and Yield: 85.0% (as a basis of a dry product).

The resulting wet cake was dried, and then subjected to an X-ray diffraction analysis with an automatic X-ray diffraction system (under a trade name: MXP 18, manufactured by MacScience. Co., Ltd.). It was found that the wet cake was a low crystalline titanylphthalocyanine having peaks at Bragg angles (2θ±0.2°) in X-ray diffraction spectrum with CuK α-ray: 7.0°, 23.5° and 25.5°. X-ray diffraction chart of the low crystalline titanylphthalocyanine is shown in FIG. 2.

Step (1-C): Preparation of the Polymorph 50.1 g of the wet cake prepared in the above step (1-B), 0.25 L of ion-exchange water, 1.75 L of THF and 1.51 kg of 0.5 mm φ glass beads were charged into a 5 L beaker. The mixture was dispersed at room temperature (25° C.) by using ThreeOne Motor (manufactured by Shinto Kagaku Co., Ltd.) and a paddle type stirring blade for 15 hours under the stirring conditions shown in the following Table 1. A sieving screen having pores, each of which has a size of 250 μm, was used to separate off the beads. The resulting dispersion was filtered under a reduced pressure.

0.2 L of THF and 0.2 L of methanol were added to and washed the resulting cake. Subsequently, 32.8 g of the obtained cake was dried at 70° C. under a reduced pressure for 24 hours. The resulting solid was pulverized with a sieving screen having pores, each of which has a size of 150 μm to give a titanylphthalocyanine having the desired polymorph. Producing amount: 12.0 g and Yield: 85.6%.

X-ray diffraction chart of the titanylphthalocyanine is shown in FIG. 1.

In addition, each intensity ratio between peaks was calculated. The results are shown in the following Table 3.

Example 2

Step (2-A): Preparation of α-type Titanylphthalocyanine

The similar procedures to those described in the above step (1-A) were conducted except that the charge amount was changed to 100 times that of the above step (1-A) to prepare the α-type titanylphthalocyanine.

Step (2-B): Acid Pasting Treatment

The similar procedures to those described in the above step (1-B) were conducted except that the charge amount was changed to 100 times that of the above step (1-B) to carry out the acid pasting treatment.

Step (2-C): Preparation of the Polymorph 502.5 g of the wet cake prepared in the above step (2-B), 2.5 L of ion-exchange water, 17.5 L of THF and 15.2 kg of 0.5 mm φ glass beads were charged into a 50 L enamel vessel. The mixture was dispersed at room temperature (25° C.) by using Traction Drive (small) (manufactured by Chuo Rika Co., Ltd.) and a propeller type stirring blade for 15 hours under the stirring conditions shown in the following Table 1. A sieving screen having pores, each of which has a size of 250 μm, was used to separate off the beads. The resulting dispersion was filtered under a reduced pressure. 2 L of THF and 2 L of methanol were added to and washed the resulting cake. Subsequently, 307.8 g of the obtained cake was dried at 70° C. under a reduced pressure for 24 hours. The resulting solid was pulverized with a sieving screen having pores, each of which has a size of 150 μm to give a titanylphthalocyanine having the desired polymorph. X ray diffraction spectrum shows an identical titanylphthalocyanine to that shown in FIG. 1. Producing amount: 118.2 g and Yield: 84.3%.

Example 3

Step (3-A): Preparation of α-type Titanylphthalocyanine

The similar procedures to those described in the above step (2-A) were conducted to prepare the α-type titanylphthalocyanine.

Step (3-B): Acid Pasting Treatment

The similar procedures to those described in the above step (2-B) were conducted to carry out the acid pasting treatment.

Step (3-C): Preparation of the Polymorph

The similar procedures to those described in the above step (1-C) of Example 1 were conducted except that the charging amount was increased to 90 times that of the above step (1-C).

4.32 kg of the wet cake prepared in the above step (3-B), 9.8 L of ion-exchange water, 80.0 L of THF and 69.3 kg of 0.5 mm φ glass beads were charged into a 200 L SUS tank. The mixture was dispersed at room temperature (25° C.) by using Traction Drive (large) (manufactured by Satake Kagakukikai Kogyo Co., Ltd.) and a paddle type stirring blade for 18 hours under the stirring conditions shown in the following Table 1. A sieving screen having pores, each of which has a size of 250 μm, was used to separate off the beads. The resulting dispersion was filtered under a reduced pressure. 10 L of THF and 10 L of methanol were added to and washed the resulting cake. Subsequently, 3.64 kg of the obtained cake was dried at 70° C. under a reduced pressure for 38 hours. The resulting solid was pulverized with a sieving screen having pores, each of which has a size of 150 μm to give a titanylphthalocyanine having the desired polymorph. X ray diffraction spectrum shows an identical titanylphthalocyanine to that shown in FIG. 1. Producing amount: 1.10 kg and Yield: 94.4%.

Example 4

Step (4-A): Preparation of (α-type Titanylphthalocyanine
The similar procedures to those described in the above step (2-A) were conducted to prepare the α-type titanylphthalocyanine.

Step (4-B): Acid Pasting Treatment
The similar procedures to those described in the above step (2-B) were conducted to carry out the acid pasting treatment.

Step (4-C): Preparation of the Polymorph
The similar procedures to those described in the above step (1-C) of Example 1 were conducted except that the charge amount was increased to 90 times that of the above step (1-C).

4.54 kg of the wet cake prepared in the above step (4-B), 9.6 L of ion-exchange water, 80.0 L of THF and 69.3 kg of 0.5 mm φ glass beads were charged into a 200 L reaction vessel applicable to an industrial sale production. The mixture was dispersed at room temperature (25° C.) by using a stirring device equipped therewith (manufactured by Tsubakimoto Chain Co.) and a paddle type stirring blade for 18 hours under the stirring conditions shown in the following Table 1. A sieving screen having pores, each of which has a size of 250 μm, was used to separate off the beads. The resulting dispersion was filtered under a reduced pressure. 10 L of THF and 10 L of methanol were added to and wash the resulting cake. Subsequently, 3.64 kg of the obtained cake was dried at 70° C. under a reduced pressure for 38 hours. The resulting solid was pulverized with a sieving screen having pores, each of which has a size of 150 μm to give a titanylphthalocyanine having the desired polymorph. X-ray diffraction spectrum shows an identical titanylphthalocyanine to that shown in FIG. 1. Producing amount: 1.18 kg and Yield: 97.6%.

Comparative Example 1

According to the examples described in JP-B-7-91486 (Patent Literature 1), 97.5 g of phthalodinitrile was added to 750 ml of α-chloronaphthalene, and then 22 ml of titanium tetrachloride was added dropwise to the mixture in a nitrogen atmosphere. After the dropwise addition was completed, the mixture was heated and reacted at 200 to 220° C. for 3 hours with stirring. Subsequently, the reaction mixture was allowed to be left and cooled, and filtered with heating at 100 to 130° C., and then the residue was washed with 200 ml of α-chloronaphthalene heated to 100° C. The resulting crude cake was vigorously washed with 300 ml of α-chloronaphthalene at room temperature, and then vigorously washed with 300 ml of methanol at room temperature, and then further vigorously washed with 800 ml of methanol, with heating, for 1 hour several times. The resulting cake was suspended into 700 ml of water to vigorously wash the cake for 2 hours with heating. pH of the filtrate was no more than 1. The vigorous washing with hot water was repeated to allow pH of the filtrate to be within a range of 6 to 7.

As a result, no titanylphthalocyanine having the polymorph according to the present invention and a mixture of α-type and γ-type crystals were obtained. X-ray diffraction spectrum of the mixture is shown in FIG. 3.

Comparative Example 2

Figure 4:
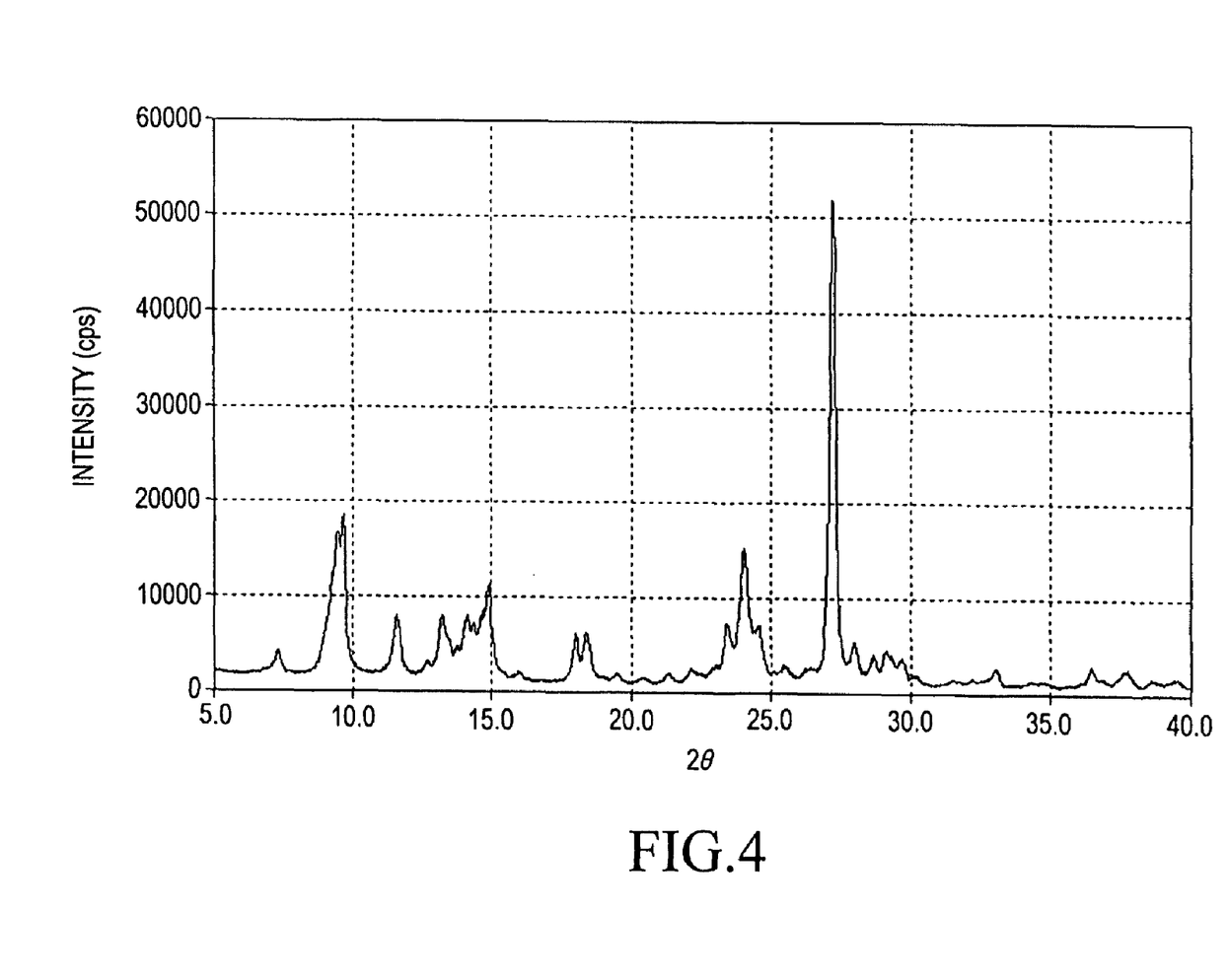
FIG. 4 is an X-ray diffraction spectrum of the titanylphthalocyanine obtained in Comparative Example 2, as a γ-type polymorph.

Comparative Example 2 employed the similar procedures to those described in Example 2 except that the 0.5 mm φ glass beads were not added among the conditions used in the above step (2-C) of Example 2. 1000.0 g of the wet cake prepared in Example 1, 5.0 L of ion-exchange water and 35.0 L of THF were charged into a 50 L enamel vessel. The mixture was dispersed at room temperature (25° C.) for 12 hours. The dispersion was filtered under a reduced pressure, and then the resulting cake was washed with 3 L of THF until the filtrate was decolorized. 699.5 g of the resulting wet cake was dried at 70° C. for 24 hours under a reduced pressure. The resulting solid was pulverized with a sieving screen having pores, each of which has a size of 150 μm to give a titanylphthalocyanine having a polymorph (in γ-type) which has peaks at the same Bragg angles (2θ) to those described in JP-B-7-91486 (Patent Literature 1). X-ray diffraction spectrum of the titanylphthalocyanine is shown in FIG. 4. Producing amount: 118.2 g and Yield: 84.3%.

Comparative Example 3

Comparative Example 3 employed the similar procedures to those described in Example 1 except that the stirring rate, among the stirring conditions used in the above step (1-C) of Example 1, was altered from 500 rpm to 300 rpm as shown in the following Table 1. The resulting titanylphthalocyanine was a conventional γ-type titanylphthalocyanine and did not have the polymorph according to the present invention.

Comparative Example 4

Comparative Example 4 employed the similar procedures to those described in Example 1 except that the stirring rate, among the stirring conditions used in the above step (1-C) of Example 1, was altered from 500 rpm to 450 rpm as shown in the following Table 1. The resulting titanylphthalocyanine was a γ-type titanylphthalocyanine and did not have the polymorph according to the present invention.

Comparative Example 5

Comparative Example 5 employed the similar procedures to those described in Example 1 except that the stirring blade, among the stirring conditions used in the above step (1-C) of Example 1, was altered as shown in the following Table 1. The resulting titanylphthalocyanine was a γ-type titanylphthalocyanine and did not have the polymorph according to the present invention.

Comparative Example 6

Comparative Example 6 employed the similar procedures to those described in Example 2 except that the stirring rate, among the stirring conditions used in the above step (2-C) of Example 2, was altered from 250 rpm to 150 rpm as shown in the following Table 1. The resulting titanylphthalocyanine was a γ-type titanylphthalocyanine and did not have the polymorph according to the present invention.

Comparative Example 7

Comparative Example 7 employed the similar procedures to those described in Example 4 except that the stirring rate, among the stirring conditions used in the above step (4-C) of Example 4, was altered from 73 rpm to 35 rpm as shown in the following Table 1. The resulting titanylphthalocyanine was a γ-type titanylphthalocyanine and did not have the polymorph according to the present invention.

The stirring conditions and the required stirring power in Examples 1 to 4 and Comparative Examples 3 to 7 are shown in the following tables.

TABLE 1

Stirring conditions and required stirring power in Examples 1 to 4 and Comparative Examples 3 to 7

| Production | | Volume of reaction vessel [L] | Stirring rate R [rpm] | Rotation rate N [sec⁻¹] | Height to liquid level H [mm] | Inner diameter of vessel D [mm] | Length of stirring blade d [mm] | Width of stirring blade b [mm] | Angle of stirring blade sinθ | Number of blades | Required stirring power P [kg-m/sec] |
|---|---|---|---|---|---|---|---|---|---|---|---|
| Examples | 1 | 5 | 500 | 8.33 | 120 | 175 | 124 | 47 | 1 | 2 | 3.17 |
| | 2 | 50 | 250 | 4.17 | 200 | 390 | 210 | 57 | 0.5 | 3 | 4.81 |
| | 3 | 200 | 85 | 1.42 | 480 | 565 | 350 | 300 | 1 | 2 | 4.32 |
| | 4 | 200 | 73 | 1.22 | 486 | 600 | 440 | 430 | 1 | 2 | 4.50 |
| Comparative Examples | 3 | 5 | 300 | 5.00 | 120 | 175 | 124 | 47 | 1 | 2 | 0.76 |
| | 4 | 5 | 450 | 7.50 | 120 | 175 | 124 | 47 | 1 | 2 | 2.36 |
| | 5 | 5 | 500 | 8.67 | 120 | 175 | 60 | 40 | 1 | 2 | 0.35 |
| | 6 | 50 | 150 | 2.50 | 200 | 390 | 210 | 57 | 0.5 | 3 | 1.13 |
| | 7 | 200 | 35 | 0.58 | 486 | 600 | 440 | 430 | 1 | 2 | 0.61 |

The required stirring power was calculated with the measured values listed in the above Table 1, density ρ: 1338 [kg/m³] and viscosity μ: 0.25 [kg/m·sec]. The calculated intermediate parameters used for the above calculation are shown in the following Table 2.

TABLE 2

Calculated intermediate parameters

| Production | A | B | p | Np |
|---|---|---|---|---|
| Example 1 | 65.80684 | 2.08075 | 2.02911 | 1.36641 |
| Example 2 | 41.40929 | 4.78891 | 1.67772 | 1.19266 |
| Example 3 | 112.36493 | 3.44123 | 2.63181 | 2.11969 |
| Example 4 | 155.11963 | 1.76288 | 1.98398 | 1.10967 |
| Comparative Example 3 | 65.80684 | 2.08075 | 2.02911 | 1.51806 |
| Comparative Example 4 | 65.80684 | 2.08075 | 2.02911 | 1.39652 |
| Comparative Example 5 | 66.41190 | 6.46201 | 1.93344 | 5.09561 |
| Comparative Example 6 | 41.40929 | 4.78891 | 1.67772 | 1.29887 |
| Comparative Example 7 | 155.11963 | 1.76288 | 1.98398 | 1.36812 |

The following Table 3 shows the intensity ratio between peaks on X-ray diffraction spectrum with respect to the titanylphthalocyanine produced in each of Examples and Comparative Examples. Herein, XRD pattern was evaluated according to the following evaluation basis:

Excellent (○): All four intensity ratios between peaks (i.e., $I_{r1}$, $I_{r2}$, $I_{r3}$ and $I_{r4}$) satisfy the ranges defined in the present invention;

Not Good (Δ): Three intensity ratios among $I_{r1}$, $I_{r2}$, $I_{r3}$ and $I_{r4}$ satisfy the ranges defined in the present invention; and Bad (x): One or two intensity ratios among $I_{r1}$, $I_{r2}$, $I_{r3}$ and $I_{r4}$ satisfy the ranges defined in the present invention.

TABLE 3

Intensity ratio between peaks

| Production | | $I_{r1}$ | $I_{r2}$ | $I_{r3}$ | $I_{r4}$ | polymorph | XRD pattern |
|---|---|---|---|---|---|---|---|
| Examples | 1 | 1.57 | 1.19 | 1.46 | 0.96 | Present inventive type | ○ |
| | 2 | 1.75 | 1.04 | 1.39 | 0.92 | Present inventive type | ○ |
| | 3 | 1.52 | 1.14 | 1.53 | 1.04 | Present inventive type | ○ |
| | 4 | 1.51 | 1.19 | 1.70 | 1.06 | Present inventive type | ○ |
| Comparative Examples | 1 | 2.08 | 0.74 | 0.51 | Non-calculable | Mixture of α- and γ-type polymorphs | X |
| | 2 | 1.61 | 0.68 | 0.95 | 0.99 | γ-type | X |
| | 3 | 1.55 | 0.69 | 0.97 | 0.95 | γ-type | X |
| | 4 | 1.48 | 0.95 | 1.22 | 0.97 | γ-type | X |
| | 5 | 1.40 | 0.73 | 1.08 | 1.00 | γ-type | X |
| | 6 | 1.52 | 0.72 | 1.01 | 0.95 | γ-type | X |
| | 7 | 1.54 | 0.71 | 1.08 | 1.00 | γ-type | X |
| Evaluation Basis | | $1.3 < I_{r1} < 1.8$ | $1.0 < I_{r2}$ | $1.3 < I_{r3} < 2.0$ | $0.9 < I_{r4} < 1.1$ | | |

These tables indicate that stirring needs a required stirring power of no less than 3.0 [kg-m/sec] to provide the titanylphthalocyanine comprising the polymorph according to the present invention. Particularly, both of Comparative Examples 3, 6 and 7, wherein stirring was conducted at a low stirring rate, and Comparative Example 5, wherein a stirring blade with a poor stirring efficiency, were employed provide a required stirring power of about 1.0 [kg-m/sec] or less than 1.0 [kg-m/sec]. In these cases, continuous stirring for no less than 100 hours can provide a known γ-type polymorph and can not provide the titanylphthalocyanine having the polymorph according to the present invention.

Subsequently, an exemplified method for producing an electrophotographic photoreceptor comprising the titanylphthalocyanine according to the present invention will be described hereinafter. Herein, the electrophotographic photoreceptor according to the present invention is not limited to these examples.

Example 5

0.2 g of the titanylphthalocyanine crystals prepared in Example 1; 0.2 g of polyvinylbutyral resin (under a trade name: Esrek BH-3, manufactured by Sekisui Chemical Co., Ltd.); 50 g of 3 mm φ glass beads; and 59.6 g of cyclohexanone were charged into a wide-mouthed bottle, and then subjected to 3 hour milling with a paint shaker to prepare a coating solution for forming a photoreceptor layer. This coating solution was applied on an aluminum plate by using a bar coater to give a film in a film thickness of 0.5 μm, and then the film was dried in air to form a charge generating layer.

Subsequently, 4.5 g of p-(N,N'-diphenylamino)benzaldehyde-N'-methyl-N'-phenylhydrazine (under a trade name: CT-501, manufactured by Fuji Photo film Co., Ltd.) as a charge transferring material (CTM); 4.5 g of a polycarbonate resin (under a trade name: Panlight L-1250, manufactured by Teijin Limited); and 51 g of methylene chloride were charged into a wide-mouthed bottle, and then ultrasonically dispersed to prepare a uniform solution. This solution was applied on the charge generating layer by using a bar coater, and then dried at 80° C. for 3 hours to form a charge transferring layer in a film thickness of 60 μm on the charge generating layer. The prepared plate is an organic photoreceptor.

Example 6

According to Example 5, an organic photoreceptor was manufactured in similar procedures to those described in Example 5 except that the titanylphthalocyanine crystals prepared in Example 1 were altered to the titanylphthalocyanine crystals prepared in Example 2.

Example 7

According to Example 5, an organic photoreceptor was manufactured in similar procedures to those described in Example 5 except that the titanylphthalocyanine crystals prepared in Example 1 were altered to the titanylphthalocyanine crystals prepared in Example 3.

Example 8

According to Example 5, an organic photoreceptor was manufactured in similar procedures to those described in Example 5 except that the titanylphthalocyanine crystals prepared in Example 1 were altered to the titanylphthalocyanine crystals prepared in Example 4.

Comparative Example 8

According to Example 5, an organic photoreceptor was manufactured in similar procedures to those described in Example 5 except that the titanylphthalocyanine crystals prepared in Example 1 were altered to the titanylphthalocyanine crystals prepared in Comparative Example 1.

Comparative Example 9

According to Example 5, an organic photoreceptor was manufactured in similar procedures to those described in Example 5 except that the titanylphthalocyanine crystals prepared in Example 1 were altered to the titanylphthalocyanine crystals prepared in Comparative Example 2.

Comparative Example 10

According to Example 5, an organic photoreceptor was manufactured in similar procedures to those described in Example 5 except that the titanylphthalocyanine crystals prepared in Example 1 were altered to the titanylphthalocyanine crystals prepared in Comparative Example 3.

Comparative Example 11

According to Example 5, an organic photoreceptor was manufactured in similar procedures to those described in Example 5 except that the titanylphthalocyanine crystals prepared in Example 1 were altered to the titanylphthalocyanine crystals prepared in Comparative Example 7.

With regard to the photoreceptors manufactured in the above-described Examples 5 to 8 and Comparative Examples 8 to 11, the electrophotographic characteristics were determined. A measuring device for electrostatic test (under a trade name: Paper Analyzer EPA-8200, manufactured by Kawaguchi Denki Co., Ltd.) was used for the measurement. Herein, charge potential (Vmax), dark decay rate (DDR) (%), residual potential (Vre.) and half decay exposure E1/2 (lux.s) (as sensitivity) were measured and evaluated, wherein each photoreceptor was initially charged at a voltage of −0.8 kV (in STAT 3 mode), allowed to be left in a dark place for 2 seconds, and then irradiated with 5.0 lux white light for 10 seconds. The measurement results are shown in the following Table 4.

The dark decay rate (DDR) (%) was determined by the following equation (9), wherein the surface potential immediately after charging ($V_0$=Vmax) and the surface potential after leaving 2 seconds in dark place ($V_2$) were measured.

$$\text{Dark decay rate}(\%) = 100 \times (V_0 - V_2)/V_0 \quad (9)$$

Evaluation

The evaluation basis for chargeability in the following table is as follows.

Excellent (⊚): Charged potential (Vmax) was −700 V or less

Good (○): Charged potential was within a range of from −700 to −600 V

Bad (x): Charged potential was −600 V or more

With respect to the evaluation basis for sensitivity, an excellent acceptable sensitivity (○) is provided in the case of the half decay exposure E1/2 (as sensitivity) of the photoreceptor is about 1.

TABLE 4

Characteristics of photoreceptor

| | CGM | Vmax | Chargeability Evaluation | DDR | Vre. | E½ | Sensitivity Evaluation |
|---|---|---|---|---|---|---|---|
| Example 5 | Example 1 | −657.3 | ○ | 6.49 | −14.3 | 0.93 | ○ |
| Example 6 | Example 2 | −735.3 | ⊙ | 6.12 | −37.0 | 1.01 | ○ |
| Example 7 | Example 3 | −755.0 | ⊙ | 7.07 | −31.3 | 1.08 | ○ |
| Example 8 | Example 4 | −724.3 | ⊙ | 6.81 | −38.3 | 0.90 | ○ |
| Comparative Example 8 | Comparative Example 1 | −495.3 | X | 10.50 | −4.7 | 0.82 | ○ |
| Comparative Example 9 | Comparative Example 2 | −535.7 | X | 7.65 | −5.3 | 1.09 | ○ |
| Comparative Example 10 | Comparative Example 3 | −504.3 | X | 9.72 | −3.3 | 0.80 | ○ |
| Comparative Example 11 | Comparative Example 7 | −506.3 | X | 9.41 | −4.7 | 0.79 | ○ |

Figure 5:
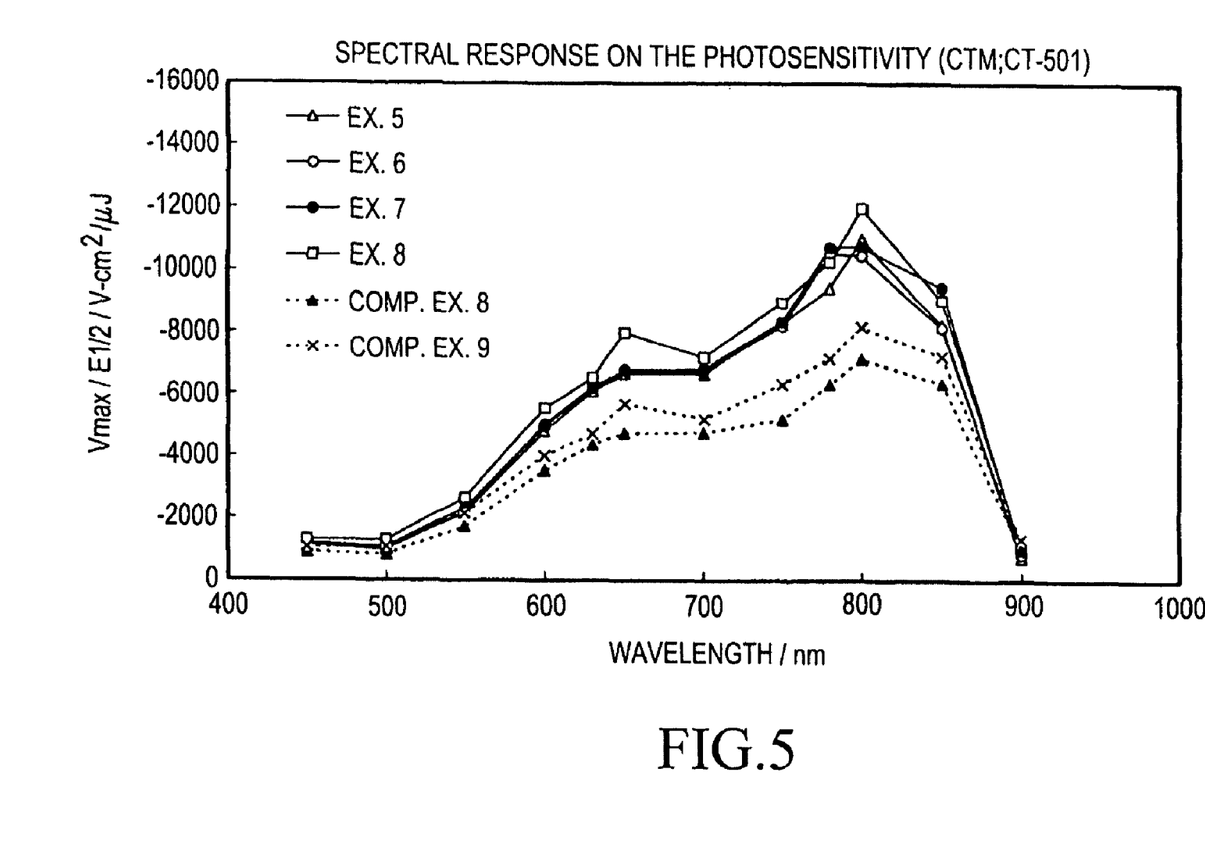
FIG. 5 shows spectral responses on the photosensitivities in Examples 5 to 8 and Comparative Examples 8 and 9.

Referring to FIG. 5 (spectral responses on the photosensitivities), all the photoreceptors in Examples have superior sensitivities to those in Comparative Examples at each wavelength. The photoreceptors of Examples have the highest sensitivities, particularly, at a wavelength within a range of from 780 to 800 nm, which range is referred to as LD and widely applicable to a light source for photocopiers, printers, etc.

Referring to the Table 4 and FIG. 5 (spectral responses on the photosensitivities), those skilled in the art will appreciate that the present electrophotographic photoreceptor comprising a charge generating material of the titanylphthalocyanine comprising the polymorph according to the present invention (see Examples 1 to 4 wherein the titanylphthalocyanine was prepared in a different scale) can provide an superior significantly improved electric characteristics to those in the Comparative Examples wherein the electrophotographic photoreceptor comprises a charge generating material of the conventional titanylphthalocyanine of γ-type polymorph.

Industrial Applicability

The present invention can provide a titanylphthalocyanine having a novel polymorph. The present invention can produce the present titanylphthalocyanine conveniently and stably even in an industrial scale. In addition, the titanylphthalocyanine according to the present invention is significantly superior to the conventional γ-type titanylphthalocyanine in the electric characteristics upon formed into an electrophotographic photoreceptor. Accordingly, the present invention can provide a charge generating material useful in the field of organic photoreceptors.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including", and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those skilled in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for producing a polymorphic form of a titanylphthalocyanine having a peak at a Bragg angle (2θ±0.2°) in X-ray diffraction spectrum with CuK α-ray: 9.0°, 9.6°, 14.1°, 14.9°, 17.9°, 18.3°, 23.4°, 24.5° and 27.2°, which includes steps of:
   (I) subjecting a titanylphthalocyanine having an α-type polymorph to an acid pasting treatment to give a titanylphthalocyanine in a form of a water-containing cake;
   (II) stirring a dispersing aid and the resulting titanylphthalocyanine in a mixed solvent of water and an organic solvent at room temperature to prepare a polymorph, wherein the stirring conditions are set to give a required stirring power of no less than 3.0 [kg-m/sec]; and
   (III) filtering, washing, and drying under a reduced pressure.

2. The method for producing the polymorphic form of the titanylphthalocyanine according to claim 1, wherein said organic solvent is tetrahydrofuran.

3. The method for producing the polymorphic form of the titanylphthalocyanine according to claim 1, wherein said dispersing aid is glass beads.

4. The method for producing the polymorphic form of the titanylphthalocyanine according to claim 1, wherein said acid pasting treatment is using a sulfuric acid.

5. The method of producing the polymorphic form of the titanylpthalocyanine according to claim 1, wherein said required stirring power is within the range of from 3.0 to 15 [kg-m/sec].

* * * * *